United States Patent [19]

Johnson et al.

[11] 4,020,119

[45] Apr. 26, 1977

[54] SELECTIVE HYDROGENATION PROCESS

[75] Inventors: Marvin M. Johnson; Donald C. Tabler; Gerhard P. Nowack, all of Bartlesville, Okla.

[73] Assignee: Phillips Petroleum Company, Bartlesville, Okla.

[22] Filed: May 5, 1975

[21] Appl. No.: 574,824

Related U.S. Application Data

[60] Division of Ser. No. 390,799, Aug. 23, 1973, Pat. No. 3,900,526, which is a division of Ser. No. 249,726, May 2, 1972, Pat. No. 3,787,511, which is a division of Ser. No. 44,665, June 8, 1970, Pat. No. 3,697,448, which is a continuation-in-part of Ser. No. 6,971, Jan. 29, 1970, abandoned.

[52] U.S. Cl. .......................... 260/677 A; 252/472; 260/677 H

[51] Int. Cl.² ......................................... C07C 11/02
[58] Field of Search .................. 260/677 A, 677 H

[56] References Cited

UNITED STATES PATENTS

| 2,511,453 | 6/1950 | Barry | 260/677 H |
| 3,743,684 | 7/1973 | Johnson et al. | 260/681.5 R |

*Primary Examiner*—Herbert Levine

[57] ABSTRACT

A method and catalysts for selective hydrogenation and isomerization which involves contacting a feedstream with hydrogen and with various supported catalysts of metallic arsenides and antimonides, with carbon monoxide being optionally introduced into the reaction as a modifier.

13 Claims, No Drawings

SELECTIVE HYDROGENATION PROCESS

This is a divisional application of our copending application having Ser. No. 390,799, filed Aug. 23, 1973, now U.S. Pat. No. 3,900,526, issued Aug. 19, 1975, which was a division of application Ser. No. 249,726, filed May 2, 1972, now U.S. Pat. No. 3,787,511, issued Jan. 22, 1974, which was a division of Ser. No. 44,665, filed June 8, 1970, now U.S. Pat. No. 3,697,448, which in turn was a continuation-in-part application of Ser. No. 6,971, filed Jan. 29, 1970, now abandoned.

This invention pertains to selective hydrogenation.

In one of its more specific aspects, this invention pertains to the use of reduced nickel arsenate on alumina catalyst for the selective hydrogenation of diolefins to the corresponding monoolefins.

Various compounds of nickel are known as active and selective hydrogenation catalysts for conversion of diolefins to monoolefins. For extended use, compounds such as nickel sulfide require the continuous addition of small amounts of sulfur to maintain catalyst activity. Such addition can create a sulfur removal problem when the selectively hydrogenated products are to be further processed in other catalytic reactors in which minute amounts of sulfur are detrimental.

There has now been discovered a selective hydrogenation catalyst which does not require the presence of objectionable sulfur-containing auxiliary materials to maintain its selectivity. This catalyst can be employed to selectivity hydrogenate diolefins to monoolefins, to double bond isomerize monoolefins in the presence of hydrogen and to hydrogenate reducible catalyst poisons such as sulfur, carbonyls, oxygen and acetylenes in the presence of monoolefins.

According to the method of this invention, there is provided a process for selectively hydrogenating polyenes to monoolefins, for isomerizing monoolefins in the presence of hydrogen and for hydrotreating olefinic streams containing minor amounts of materials such as compounds of sulfur, carbonyls, oxygen, and acetylene which comprises contacting the stream comprising at least one of the aforementioned materials with hydrogen and with an afterdescribed catalyst under reaction conditions.

According to this invention, the aforementioned contact is made with a catalyst comprised of a metal selected from the group consisting of iron, cobalt and nickel in the form of its arsenide or antimonide derivatives, or mixtures thereof.

Accordingly, it is an object of this invention to provide a simply prepared catalyst which possesses sustained activity.

It is another object of this invention to provide a selective hydrogenation process which is resistant to typical catalyst poisons and which can be used for sustained periods without requiring regeneration.

The method of this invention is broadly applicable to the selective hydrogenation of olefinic feedstocks. The process is selective because it provides a method of hydrogenating materials such as acetylenic compounds, organic sulfur compounds, organic peroxides, carbonyl compounds, cyclic and acyclic polyenes, and the like. However, the process is without substantial activity for the hydrogenation of monoolefins. In some instances, no hydrogenation of monoolefins is detectable.

When applied to a cyclic or acyclic polyene, the process selectively hydrogenates these to cyclic or acyclic monoolefins with substantial selectivity depending upon the specific feeds, catalysts, and conditions used. Similarly, feedstreams which contain substantial amounts of monoolefins can be effectively hydrotreated to hydrogenate minor amounts of impurities, e.g., acetylenes, dienes, sulfur compounds, without significant conversion of the monoolefins to saturates. Thus, the invention is applicable for hydrogenating olefinic feedstocks where monoolefins are a substantial portion of the product. These product monoolefins can be present in the feed, or can be produced within the reaction zone as a hydrogenation product from a more unsaturated olefinic compound.

The olefinic feedstocks can be diluted with nonhydrogenatable or inert diluents. Olefinic refinery streams can be used as feedstocks.

Applicable polyenes are those olefinic hydrocarbons which have more than one double bond per molecule. For purposes of this invention, acetylenic hydrocarbons are also included in this scope, because both acetylenes and dienes, for example, can be selectively hydrogenated to monoolefins. In general, any polyene, capable of being hydrogenated, can be selectively hydrogenated by the process of this invention. As a matter of practical commercial application, polyenes having up to about 15 carbon atoms per molecule are preferred. Some examples of these are acetylene, 1,3-pentadiene, 1,5-cyclooctadiene, 1,3,7-octatriene, 4-vinylcyclohexene, 1,4,9-decatriene, 1,5,9-cyclododecatriene, 2-hexyne, 3,4-dimethyl-1,6-tridecadiene, and the like, and mixtures thereof.

Similarly, the monoolefins which can be subjected to the process of the present invention for hydrotreatment of impurities and/or double bond isomerization include any such cyclic or acyclic olefins which are normally hydrogenatable. As a practical matter, monoolefins of up to about 15 carbon atoms per molecule are of commercial importance and are preferred. Some examples of these are ethylene, propylene, butene-1, pentene-1, heptene-2, 4-methylpentene-1, 3-ethylcyclohexene, decene-5, octene-1, 4-ethyl-6-tridecene, and the like, and mixtures thereof.

As mentioned, the catalysts are the arsenide or antimonide forms of iron, cobalt, and nickel. In its preferred form, the catalyst of this invention is a supported, reduced nickel arsenide. Such nickel-arsenic combinations as are satisfactory have the empirical formula $NiAs_x$, in which $x$ can have a value from about 0.33 to about 2.0, preferably 0.6 to 1.0, and includes nickel arsenide compounds such as $NiAs$, $NiAs_2$, and $Ni_3As_2$. However, the proportions of nickel and arsenic need not be stoichiometric; an excess of either the nickel or the arsenic can be present.

If the nickel is employed in its antimonide form, the combination will have the empirical formula $NiSb_x$, in which $x$ can have a value of from about 0.33 to about 2.0, preferably 0.6 to 1.0. Suitable forms are $NiSb$, $NiSb_2$, $Ni_3Sb$, $Ni_5Sb_2$, $Ni_7Sb_3$, $Ni_2Sb_3$, and $Ni_3Sb_5$. The proportions of nickel and antimony need not be stoichiometric. Generally, the nickel is employed in the form of $NiY_x$ in which Y is arsenic or antimony and $x$ has a value from about 0.33 to about 2.0, preferably about 0.6 to about 1.0.

If cobalt and iron are substituted for nickel, the same empirical formula applies.

Generally then, the catalysts of this invention have the formula $MY_x$ in which M is a metal selected from the group consisting of nickel, cobalt, and iron, Y is arsenic or antimony and $x$ has a value from about 0.33 to about 2.0, preferably about 0.6 to about 1.0. Because of its greater selectivity, Y is preferably arsenic.

For purposes of this disclosure, the invention will be most frequently explained in terms of the nickel arsenide catalyst without meaning to limit the invention thereto. All uses and applications of any one of the catalysts specifically designated are intended to apply to all of the catalysts which are the subject of this invention.

While a supported type catalyst is preferred, the catalyst can also be employed in a nonsupported state as, for example, in the form in which the principal components are coprecipitated from a sol.

In its supported state, any conventionally employed nonacidic or relatively nonacidic catalyst support can be used. Preferably supports include gamma-alumina, alpha-alumina, silica, magnesia, charcoal, calcium aluminate, natural or synthetic molecular sieves and their combinations. In general, the granular support will have a surface area of about 1 to about 400 square meters per gram.

In the preparation of the catalysts, the nickel and arsenic, or antimony, can be simultaneously deposited on the support as, for example, by precipitating nickel arsenate or nickel antimonate on the support; or the support can be impregnated with the nickel and the arsenic, or antimony, in individual treatments. In either instance, sufficient nickel is employed to deposit about 0.1 to about 20, preferably from about 0.5 to about 10, weight percent nickel on the support and sufficient arsenic or antimony is employed so as to produce a finished catalyst containing from about 0.05 to about 50 weight percent, preferably 1.0 to 10 weight percent, arsenic or antimony.

Thus, the catalyst can be prepared by impregnation of a suitable catalyst support with a water soluble salt, such as a nitrate, halide, etc. of nickel, cobalt, or iron. The impregnated support can then be calcined and re-impregnated with an aqueous solution of, for example, ammonium arsenate prepared by dissolving arsenic trioxide in ammonia-water.

Under any method of preparation the base, after deposition thereon of the materials concerned, can be washed to remove undesirable soluble salts, dried, calcined in air, and then reduced with hydrogen at any suitable temperature and pressure which is sufficient to produce the active nickel arsenide or antimonide. For example, hydrogen reduction at atmospheric pressure at 500° to 800° F for 0.1 to 20 hours can be used. In some instances, the calcination in air step can be omitted.

The catalysts of the present invention have no appreciable skeletal isomerization ability; that is, when contacted with straight chain monoolefins or polyenes under the reaction conditions specified, they promote little branching of the molecule. Since the skeletal isomerization ability of a supported catalyst is generally a function of its acidity, which is largely contributed by the support, the use of acidic supports which promote skeletal isomerization is to be avoided and nonacidic supports are preferred. This is due to the fact that such acidic supports do not give the selective hydrogenation results of the present invention. However, some mildly acidic supports, such as the flame-hydrolyzed aluminas, are satisfactory for use in the present invention if their acidic character is minimized or destroyed during the catalyst preparation. Accordingly, ammoniacal solutions or basic precipitants are preferentially employed in preparing the catalysts since the former act to reduce the acidity of the support, to avoid skeletal isomerization activity, and to provide a selective hydrogenation catalyst.

The conditions under which the method of this invention is employed, whether for selective hydrogenation or poison removal by hydrogenation, can vary widely. Generally, the reactions are conducted by passing the hydrocarbon stream, as a vapor, with hydrogen into contact with catalyst, the reaction zone being maintained at a temperature of from about 75° F to about 750° F, preferably from about 200° F to about 600° F, at a pressure of from about atmospheric to about 1,000 psig. The hydrocarbon stream is passed in contact with the catalyst at a rate sufficient to provide a liquid hourly space velocity (LHSV) of from about 0.1 to about 10. Hydrogen is introduced at a rate which provides a hydrogen to feed molar ratio of from about 0.1 to 1 to about 5 to 1.

The selectivity of the process and catalyst of this invention can be improved by incorporating carbon monoxide in the feedstock. Carbon monoxide in amounts of about 50–100,000 ppm, preferably from about 500 to about 5,000 ppm, of the feedstream have been found to be effective. The carbon monoxide can be introduced with the feedstock, with hydrogen or it can be separately introduced.

The catalysts of this invention can be regenerated in a number of ways including conventional calcination in diluted air. Inasmuch as the reaction conditions to which these catalysts are subjected are relatively mild, catalyst regeneration can be primarily directed to the removal of viscous oil deposits. Accordingly, the catalysts can be regenerated by removing these deposits by oxidation or by washing with a liquid aromatic solvent under conditions suitable for removing the deposits. Preferably, benzene, toluene, xylene, and mixtures thereof are passed through the catalyst bed at a temperature such as 200°–250° F, the bed being thereafter flushed with warm hydrogen or an inert gas.

The catalysts of the present invention, particularly in the nickel arsenide form, are suitable under the reaction conditions previously set forth, for the double bond isomerization of monoolefins. Best results are obtained at 350°–600° F, preferably at 400°–500° F. In this application, nonacidic supports are employed. An amount of hydrogen sufficient to keep the catalyst unimpaired, or clean, is employed. Carbon monoxide can also be included in the feed.

The following examples indicate methods of preparing the catalysts of this invention and their employment in the method of this invention.

EXAMPLE I

A nickel arsenide catalyst was prepared by impregnating a catalytic grade alumina gel base with sufficient nickel sulfate to provide 4.25 weight percent nickel based on the weight of the alumina. The nickel-impregnated alumina was then impregnated with a stoichiometric amount of sodium arsenate. The impregnated base was then washed to remove soluble salts, dried and reduced with hydrogen at atmospheric pressure and at a temperaure of about 520° to 600° F for one and one-half hours to form the catalyst, which contained a nominal $Ni_3As_2$ composition.

EXAMPLE II

A nickel arsenide catalyst was prepared as follows: 98.5 grams of nickel nitrate, $Ni(NO_3)_2 \cdot 6H_2O$, were dissolved in 1200 ml of distilled water and 150 g of finely divided, flame-hydrolyzed alumina were added to the solution to produce a slurry. To this slurry, 32.1 grams of arsenic acid, $H_3AsO_4$, dissolved in 300 ml of distilled water were added. The resulting slurry was neutralized with ammonium hydroxide to a pH of 7.

The mixture was filtered and the solids were washed with distilled water, refiltered, dried, and heated to 1000° F at which temperature they were maintained for two hours. The solids were then ground and screened and 95 grams of a 9 to 20 mesh catalysts were recovered. This catalyst contained 9.8 percent nickel, 9.1 percent arsenic, had a surface area of 70 m²/gm and a pore volume of 0.63 cc/gm. Before use, the catalyst is reduced in the presence of hydrogen at 520° to 600° F.

EXAMPLE III

A charcoal-based catalyst was prepared by impregnating 6/14 mesh coconut charcoal with a nickel acetate solution. The impregnated charcoal was dried at 250° F and impregnated with $H_3AsO_4$, dried at 250° F and washed with aqueous ammonia. Activation was accomplished by heating at 800° F in hydrogen for two hours, the air calcination step being omitted. The catalyst is active for selective hydrogenation of polyenes.

EXAMPLE IV

Due to the solubility of most antimony compounds, different techniques were used to make the antimony-containing catalysts. One suitable method was to dissolve antimony trioxide ($Sb_2O_3$) in a water solution of tartaric acid containing a small amount of nitric acid. This step formed an antimonyl tartrate compound. The required amount of nickel acetate or nickel nitrate was then dissolved in the tartrate solution to form a clear green solution both nickel and antimony. This solution was then used to impregnate the preformed catalyst base pellets, which were dried, and then calcined in air at 900° to 1000° F to remove the organic portion of the impregnating compound. The calcined catalyst was then heated in a stream of hydrogen at 500° to 900° F, after which it was ready to use.

Similar methods to the above have been employed to support both nickel-arsenide and nickel-antimonide on magnesia silica, Celite, and calcium aluminate ($CaAl_2O_4$) supports, the resulting catalysts in all instances being effective for selective hydrogenation.

EXAMPLE V

The catalyst prepared in Example I was employed for the selective hydrogenation of a stream comprised of substantial amounts of 4-vinylcyclohexene incyclohexane diluent. The conditions under which the run was conducted, and the selective hydrogenation effected, are indicated by the following:

| Stream | Product from Selective Hydrogenation with Nickel Arsenide on Alumina (4.25% Ni) |
|---|---|
| Operating Conditions | |
| Temperature, ° F | 534 |
| Pressure, psig | 100 |
| Liquid Hourly Space Velocity (LHSV) | 2 |
| Product Analysis, Wt. % (Diluent Free) | |
| Ethylcyclohexane | 10.7 |
| 1-Ethylcyclohexene | 51.6 |
| 4-Ethylcyclohexene | 5.9 |
| 3-Ethylcyclohexene | 15.7 |
| Ethylbenzene | 12.2 |
| 4-Vinylcyclohexene | 0 |
| Ethylidenecyclohexane | 3.9 |

These data indicate that the catalyst and method of this invention are effective in selectively hydrogenating 4-vinylcyclohexene to primarily monoolefinic compounds.

EXAMPLE VI

The following illustrates the effectiveness of the method and catalyst of this invention in hydrotreating a stream of mixed monoolefins. This mixture of polymerized lower olefins (cat poly-gasoline) was used as a feedstock to an olefin disproportionation reaction to produce isoamylenes for isoprene manufacture. This stream was hydrogenated for the purpose of reducing the concentrations of certain undesirable materials such as sulfur compounds and carbonyl compounds such as aldehydes and ketones. Operating conditions and results are presented when employing a nickel arsenide catalyst similar to that prepared in Example I.

| Operating Conditions | | |
|---|---|---|
| Temperature, ° F | | 475 |
| Hydrogen Pressure, psig | | 100 |
| Liquid Hourly Space Velocity | | 2.7 |
| Stream | Feed | Product |
| Carbonyls, ppm | 115 | 2 |
| Sulfur, ppm | 7 | 5 |
| Saturated, wt. % | 3.3 | 3.7 |
| Maleic Anhydride Value | 5.2 | 4.6 |

The above data illustrate that the method and catalyst of this invention reduced the sulfur, conjugated diene and carbonyl concentration of the highly olefinic feedstream without significant increase in saturates.

EXAMPLE VII

The following example illustrates the results of hydrotreating a heptene feed stream with the catalyst and by the method of this invention. This heptene stream had an IBP of 181° F, and EP of 251° F, and contained 24.9 percent cycloolefins and straight chain diolefins, 3.1 percent cyclodiolefins and 35.6 percent monoolefins. It was hydrotreated with the catalyst prepared in Example I for diolefin conversion to monoolefins and for sulfur reduction. Feedstream analysis, operating conditions and product stream analyses were as follows:

| Operating Conditions | | |
|---|---|---|
| Temperature, ° F | | 510 |
| Hydrogen Pressure, psig | | 100 |
| Liquid Hourly Space Velocity | | 2.5 |
| Stream | Feed | Product |
| Sulfur, ppm | 253 | 95 |
| Maleic Anhydride Value | 28.7 | 6.0 |
| Saturates, Wt. % | 28.2 | 29.3 |

These data indicate a significant reduction in sulfur content and in diolefin content. The increase in saturate content is nonsignificant since the values are within the accuracy of the test method employed.

EXAMPLE VIII

The method and catalyst of this invention are effective for selective hydrogenation of 1,5-cyclooctadiene to cyclooctene as shown by the following series of runs in which cyclooctadiene was passed with hydrogen over a catalyst comprising 8.6 weight percent nickel and 8.6 weight percent arsenic on an alumina base.

The nickel arsenide catalyst was 20/40 mesh and had a surface area of 83 m²/g and a pore volume of 0.73 ml/g. In all instances, carbon monoxide was introduced into the reaction and had the effect, as previously mentioned, of modifying the extent to which the selective hydrogenation took place.

runs were made under comparable conditions, the carbon monoxide being introduced into the reactor as a gas with the feed in both instances. Results were as follows:

| Run No. | I | II |
|---|---|---|
| Carbon Monoxide Introduced | Yes | No |
| Reaction Conditions | | |
| Pressure, psig | 365 | 365 |
| Temperature, ° F | 230, steady | 230 - rising to 520 in 1½ hours |
| Gaseous Hourly Space Velocity | 5000 | 5000 |
| Feed Analysis, Vol. % | | |
| Hydrogen | 80 | 80 |
| Ethylene | 20 | 20 |
| Acetylene, ppm | 540 | 540 |
| Carbon Monoxide (ppm) | 540 | 0 |
| Product Analysis* | | |
| Acetylene | <1 ppm | <1 ppm |
| Ethane, wt. % | 0.2 | 30% after 20 minutes reaction time |

*Hydrocarbon basis.

The results indicate that the addition of carbon monoxide improves the selectivity of the method and the catalyst for the hydrogenation of acetylene in preference to ethylene. In the absence of CO, more ethylene was destroyed as evidenced by the analysis and the temperature rise.

In other runs the use of carbon monoxide has been found to produce similar results with the other catalysts

| Run No. | I | II | III | IV | V | VI |
|---|---|---|---|---|---|---|
| Catalyst, Quantity, gms | 13.9 | 13.9 | 13.9 | 13.9 | 13.9 | 13.9 |
| Reaction Pressure, psig | 100 | 100 | 200 | 200 | 300 | 300 |
| Reaction Temperature, ° F | 360 | 360 | 360 | 360 | 360 | 360 |
| Feed Rate, mols/hr. | | | | | | |
| Hydrogen | 0.954 | 0.448 | 1.10 | 0.563 | 1.050 | 1.080 |
| Carbon Monoxide | 0.046 | 0.022 | 0.053 | 0.027 | 0.052 | 0.053 |
| Cyclohexane | 0.599 | 0.602 | 0.569 | 0.255 | 0.251 | 0.602 |
| 1,5-Cyclooctadiene | 0.052 | 0.053 | 0.049 | 0.018 | 0.022 | 0.052 |
| $C_8$ Product Distribution, % | | | | | | |
| Cyclooctane | 1.25 | 1.09 | 2.39 | 7.10 | 8.64 | 2.94 |
| Cyclooctene | 97.60 | 97.68 | 97.60 | 92.89 | 91.36 | 97.06 |
| 1,3-Cyclooctadiene | 1.13 | 1.19 | 0.01 | 0.01 | <.01 | <.01 |
| 1,4-Cyclooctadiene | 0.07 | 0.03 | <.01 | <.01 | <.01 | <.01 |
| 1,5-Cyclooctadiene | 0.06 | 0.01 | <.01 | <.01 | <.01 | <.01 |

These data illustrate that the invention catalyst inhibited with carbon monoxide shows excellent selectivity and that it is possible to reduce diolefin content to less than 0.05 percent and maintain excellent selectivity to cyclooctene. Under these conditions in the absence of CO conversion of cyclooctadiene to cyclooctane was typically 18–20 percent.

The selective hydrogenation of cyclooctadiene, as shown above, has been effectively carried out in runs of up to 80 hours in duration. This demonstrates the highly desirable long-lived characteristic of this catalyst system and process.

The effect of the addition of carbon monoxide is also shown in the employment of the method and catalyst of this invention for the selective hydrogenation of acetylene.

EXAMPLE IX

The following runs, in which streams containing acetylene and ethylene were hydrogenated with, and without, the presence of carbon monoxide, were conducted employing a nickel arsenide agent on alumina, the quantities of nickel and arsenic being 8.3 and 7.6 weight percent of the total catalyst, respectively. The of this invention. This has been particularly true of nickel arsenide on alumina for selectively hydrogenating acetylene in ethylene during operating periods of up to about 600 hours.

The introduction of carbon monoxide into the reaction zone is also effective in improving the selectivity when hydrogenating diolefins to monoolefins in respect to minimizing the extent of monoolefin hydrogenation. This is illustrated by the following example involving the selective hydrogenation of 1,5-cyclooctadiene to cyclooctane at various levels of carbon monoxide concentration in the reaction zone.

EXAMPLE X

Each of the following hydrogenations was conducted in the presence of 10 g. of an alumina-supported nickel arsenide catalyst containing 8.3 weight percent nickel and 7.6 weight percent arsenic. The feedstream comprises 1,5-cyclooctadiene in n-pentane diluent, hydrogen and carbon monoxide. The 1,5-cyclooctadiene comprised 6.6 mole percent of the total hydrocarbon in the reaction mixture. The concentration of carbon monoxide in relation to the moles of 1,5-cyclooctadiene was the only significant factor varied. Results were as follows:

and returned to service. The results of the hydrogenation using the washed catalyst were as follows:

| Run No. | Reactor Temp., °F. | Reactor Press., psig | Mols, 1,5-Cyclooctadiene per Mole of CO | Hydrogen Moles per Hour | Hydrocarbon Moles per Hour | Product Distribution Wt. % | | | | |
|---|---|---|---|---|---|---|---|---|---|---|
| | | | | | | Cyclooctadiene | | | Cyclooctene | Cyclooctene |
| | | | | | | 1.5 | 1.4 | 1.3 | | |
| 1 | 400 | 100 | 7.0 | 0.94 | 0.415 | 18.9 | 14.7 | 35.8 | 28.0 | 2.5 |
| 2 | 400 | 200 | 7.0 | 0.74 | 0.36 | 11.2 | 11.5 | 33.8 | 40.8 | 2.7 |
| 3 | 400 | 400 | 7.0 | 0.79 | 0.420 | 1.2 | 0.7 | 3.1 | 90.6 | 4.5 |
| 4 | 400 | 400 | 3.5 | 0.82 | 0.268 | 0.4 | 0.4 | 4.1 | 92.0 | 3.0 |
| 5 | 430 | 400 | 3.5 | 1.06 | 0.296 | 0.2 | 0.1 | 0.4 | 92.7 | 6.7 |

These data show that carbon monoxide prevents runaway conversion to cyclooctane and illustrate an increasing selectivity in the conversion of the cyclooctadiene to cyclooctene with an increase in carbon monoxide to 1,5-cyclooctadiene ratio. This is particularly evident at higher reactor pressures as shown by comparison of Run 3 with Run 4.

The selective hydrogenation of cyclooctadiene has been carried out with the various catalysts of this invention in runs of up to 80 hours in duration.

As mentioned, the method and catalysts of this invention are also suitable for the double bond isomerization of monoolefins. The following is illustrative of this.

EXAMPLE XI

A catalyst comprising nickel arsenide on alumina, prepared in accordance with one of the previously described methods, was contacted with a mixture comprising 10 percent pentene-1 and 90 percent cyclohexane at the rate of 3.1 volumes of feed per hour per volume of catalyst. Hydrogen and carbon monoxide were introduced into the reaction zone, as a mixture containing 2 percent carbon monoxide in hydrogen, at a rate of 600 volumes of the mixture per hour per volume of catalyst. Initial reaction conditions were 375° F and 100 psig. Under these conditions, 15 percent of the pentene-1 was converted to cis- and trans-pentene-2 isomers.

The reaction conditions were then altered to 475° F and 200 psig, under which conditions an equilibrium mixture of double bond isomers of pentene was produced, at which point the reaction mixture was comprised of about one part pentene-1, about three parts cis-pentene-2 and about six parts transpentene-2. Only two percent of the original pentene had been hydrogenated to pentane.

In the double bond isomerization of monoolefins as described above, the presence of carbon monoxide has also been found effective in limiting the extent to which hydrogenation takes place. Further, because of its relative insensitivity to typical catalyst poisons, such a process is capable of long operating periods between regenerations.

One acceptable procedure for regenerating the catalyst by solvent washing is described in the following.

EXAMPLE XII

A bed of contaminated nickel arsenide on alumina catalyst, which had become spent in the selective hydrogenation of acetylenes in ethylene in accordance with the method of this invention, was washed with toluene and a viscous residue amounting to about 18 percent of the catalyst was washed from it. The catalyst was then blown substantially dry with warm flue gas and returned to service. The results of the hydrogenation using the washed catalyst were as follows:

| | Spent Catalyst After Regeneration By Extraction |
|---|---|
| Feed Rate, Hourly Space Velocity | 6000 |
| Operating Temperature, ° F | 230 |
| Operating Pressure, psig | 350 |
| Feed Analysis, Mole % | |
| Hydrogen | 77.8 |
| Ethylene | 22.1 |
| Acetylene | 0.078 |
| Carbon Monoxide | 0.073 |
| Product Analysis, Mole % | |
| Acetylene, ppm | 7 |
| Ethane, mole % | 0.21 |
| Conversion | |
| Acetylene, Mole % | 99.1 |
| Ethylene to Ethane, Mole % | 0.95 |

These data indicate the effectiveness of the extraction method of catalyst regeneration employable with the method and catalyst of this invention in restoring the selective hydrogenation ability of the catalyst.

Prior to its restoration by solvent washing, the spent catalyst had little or no activity at 230° F. When the temperature was increased to improve the activity, a runaway reaction occurred with an uncontrollable temperature increase up to about 440° F. About 50 percent of the ethylene was then being converted to ethane.

EXAMPLE XIII

Cyclododecatriene was selectively hydrogenated to cyclododecene over a relatively low surface area alumina-supported nickel arsenide catalyst. The catalyst contained 9.0 weight percent nickel, 9.7 weight percent arsenic and had a surface area of 14.8 m²/g. A 10 weight percent mixture of cyclododecatrieno in cyclohexane diluent was hydrogenated during passage through a fixed bed of this catalyst. The temperature was 410° F, the pressure was 100 psig, and the feed rates for the cyclododecatriene, hydrogen and carbon monoxide were $8.09 \times 10^{-4}$, $3.61 \times 10^{-2}$, and $7.4 \times 10^{-4}$ moles per hour-gram of catalyst, respectively. The results of the run are shown by the analysis of the $C_{12}$ compounds in the effluent:

| $C_{12}$ Product | Wt. % |
|---|---|
| Cyclododecene | 85.4 |
| Cyclododecane | 10.1 |
| Bicyclics | 4.5 |
| Cyclododecatriene | 0.0 |

These data illustrate that the cyclododecatriene was completely converted. Also, they indicate that the cyclic triene was very selectively converted to the cyclic monoolefin with little complete hydrogenation of the cyclic triene to the saturated compound and with only a minor amount of bicyclic formation.

It has been found that iron arsenides are particularly effective in converting acetylenes to monoolefins or to polymers in the presence of diolefins with substantially no conversion of the diolefins themselves. Similarly, iron arsenides are effective in converting acetylenes to monoolefins in the presence of diolefins and monoolefins without substantial conversion of either the diolefin or monoolefin.

The iron arsenide catalysts can be prepared in a number of ways which embody the same general principles embodied in the preparation of the nickel catalyst. That is, the iron and arsenic, or antimony, can be simultaneously deposited on the support by precipitation or the support can be impregnated with the iron and arsenic or antimony from suitable solutions. In any instance, the ferric or ferrous iron is employed to deposit about 0.1 to about 20, preferably from about 0.5 to about 10, weight percent iron on the support and sufficient arsenic or antimony is employed so as to produce a finished catalyst containing from about 0.05 to about 50 weight percent, preferably 1.0 to 10 weight percent, arsenic or antimony.

The following methods of preparation are illustrative of but two of these.

In one preparation of iron arsenide catalysts, 104 g of a pilled commercial gamma-alumina catalyst were immersed in an aqueous solution of ferric nitrate and arsenic acid, prepared by dissolving 15 g of Fe($NO_3$)$_3$·$9H_2O$ and 6 g of $H_3AsO_4$ in 150 ml of deionized water. After two hours of contact, the pills were then calcined in air at 1000° F for four hours after which they were contacted with hydrogen at 800° F for four hours to reduce the ferric arsenate to iron arsenide.

In another preparation of the iron arsenide catalyst, 6 g of $H_3AsO_4$ were dissolved in 150 ml of water. Seventeen and six-tenths grams (17.6 g) of $FeSo_4$·$7H_2O$ were dissolved in 150 ml of water. The two solutions were combined and 50 g of Alon-C alumina were mixed with the solution. Ammonia was added to the mixture until the mixture had a pH of 8. At this pH, ferrous arsenate precipitated out and the precipitated ferrous arsenate and Alon-C alumina were separated from the liquid and dried. The solids were then calcined in air at 1000° F. for 1 hour after which they were contacted with hydrogen at 800° F for about 16 hours to reduce the ferrous arsenate to iron arsenide.

Conversions employing the aforementioned iron catalysts were conducted using a refinery-produced butadiene concentrate with both catalysts. The $C_4$ fraction of this concentrate had the following composition by gas liquid chromatography:

| Component | Mole %, $C_4$ Basis |
|---|---|
| n-Butane | 34.65 |
| 1-Butene & Isobutene | 12.56 |
| t-2-Butene | 3.54 |
| c-2-Butene | 2.83 |
| 1,3-Butadiene | 45.62 |
| 1,2-Butadiene | 0.17 |
| 1-Butyne | 0.08 |
| Vinylacetylene | 0.54 |
| 2-Butyne | 0.01 |
| | 100.00 |

In the employment of the iron arsenide catalyst prepared from ferric arsenate, according to the method of this invention, the reaction was conducted at 250° F and 500 psig at a butadiene concentrate WHSV of 0.6 and a hydrogen CHSV of 560. Analysis of the product was as follows:

| Component | Mole Percent, $C_4$ Basis |
|---|---|
| n-Butane | 35.41 |
| 1-Butene & Isobutene | 12.07 |
| t-Butene-2 | 2.11 |
| c-Butene-2 | 3.29 |
| 1,3-Butadiene | 47.12 |
| 1,2-Butadiene | — |
| 1-Butyne | — |
| Vinylacetylene | — |
| 2-Butyne | — |
| | 100.00 |

These data indicate that all of the $C_4$ acetylenes and all of the 1,2-butadiene had been hydrogenated with no loss of 1,3-butadiene.

In the employment of the iron arsenide catalyst prepared from ferrous arsenate, according to the method of this invention, the reaction was conducted at 315° F and 600 psig at a butadiene concentrate WHSV of 2.0 and a hydrogen CHSV of 500. Analysis of the product was as follows:

| Component | Mole Percent, $C_4$ Basis |
|---|---|
| n-$C_4H_{10}$ | 38.00 |
| Butene-1 & Isobutene | 13.50 |
| t-Butene-2 | 3.71 |
| c-Butene-2 | 3.47 |
| 1,3-Butadiene | 41.09 |
| 1,2-Butadiene | 0.19 |
| 1-Butyne | 0.03 |
| Vinylacetylene | 0.00 |
| 2-Butyne | 0.01 |
| | 100.00 |

These data indicate that all of the vinylacetylene had been hydrogenated with a 12 percent loss of 1,3-butadiene by hydrogenation.

It will be noted that the method of this invention employing the iron-containing catalysts can be carried out at somewhat lower temperatures than those temperatures previously defined for the nickel catalysts converting diolefins to monomers, that is, at temperatures from about 200° to about 400° F.

The aforementioned butadiene concentrate was contacted with a nickel arsenide catalyst and hydrogen for the purpose of carrying out those conversions conducted with the iron arsenides. This nickel arsenide catalyst had been prepared by dissolving 98.5 g Ni($NO_3$)$_2$·$6H_2O$ in 1200 ml of water to which were added 150 g Alcon-C alumina to make a slurry. To the slurry were added 32.1 g $H_3AsO_4$ in 300 ml $H_2O$ giving a slurry of pH 1.6. Ammonium hydroxide was added until pH 7 when $Ni_3(AsO_4)_2$ precipitated. The slurry was then filtered, washed with water and filtered again. The slurry was then heated 16 hours at 212° F; the catalyst was calcined at 1000° F for 30 minutes after which it was cooled, ground and sieved to 10/20 mesh. The catalyst had an arsenic content of 8.6 weight percent, a surface area of 83 m²/gm and a pore volume of 0.73 ml/g.

In a first run conducted at 200 psig, 218° F, a butadiene concentrate feed rate of 1.4 WHSV and a hydrogen feed rate of about 600 CHSV, all of the acetylenes and all but a trace of 1,2-butadiene were hydrogenated.

However, about twelve percent of the 1,3-butadiene was also hydrogenated.

It will be evident from the foregoing that various modifications can be made to the method of this invention. However, such are considered as being within the scope of the invention.

We claim:

1. A process for hydrotreating an acyclic monoolefin feedstream containing undesirable materials including acetylenic compounds, organic sulfur compounds, carbonyl compounds, diolefins, and other unsaturated impurities to selectively hydrogenate said undesirable materials which comprises contacting hydrogen and said feedstream under hydrogenation conditions with a catalyst consisting essentially of an arsenide having empirical formula $MAs_x$, M being iron, or cobalt and $x$ being a number from about 0.6 to about 1.0 at an elevated temperature sufficient to selectively hydrogenate and remove a substantial portion of said undesirable materials present in said feedstream without significant conversion of acyclic monoolefin to saturates and recovering said acyclic monoolefin feedstream substantially reduced in said undesirable materials.

2. A process according to claim 1 in which said catalyst is supported on a material selected from the group consisting of nonacidic gamma-alumina, silica, magnesia, charcoal, calcium aluminate, and natural and synthetic molecular sieves and in which the metal is present on said support in an amount from about 0.1 to about 20 weight percent.

3. A process according to claim 1 wherein the contacting includes a temperature of from about 75° F to about 750° F, a pressure of from about atmospheric to about 1,000 psig, and a hydrogen to feed ratio of 0.1 to 1 to 5 to 1, and the contacting is effected under vapor phase conditions.

4. A process according to claim 1 wherin the catalyst is ferric arsenide, or ferrous arsenide.

5. A process according to claim 1 for the hydrogenation of an acyclic monoolefin feedstream also containing acetylene wherein the selectivity for the conversion of acetylenes without substantial hydrogenation of the monoolefin to produce a substantially acetylene-free monoolefins stream is accomplished by carrying out the hydrogenation in the presence of added carbon monoxide.

6. A process according to claim 1 wherein the contacting includes a temperature of from about 200° to about 400° F, a pressure of from about atmospheric to about 1,000 psig, and a hydrogen to feed ratio of 0.1 to 1 to 5 to 1, and the catalyst is ferric or ferrous arsenide.

7. A process according to claim 1 for hydrotreating feedstreams containing acyclic monoolefins having up to about 15 carbon atoms per molecule.

8. A process for hydrotreating an acyclic monoolefin feedstream containing undesirable materials including acetylenic compounds, organic sulfur compounds, carbonyl compounds, diolefins, and other unsaturated impurities to selectively hydrogenate said undesirable materials which comprises contacting hydrogen and said feedstream under hydrogenation conditions with a catalyst consisting essentially of an arsenide of iron, or cobalt at an elevated temperature sufficient to selectively hydrogenate and remove a substantial portion of said undesirable materials present in said feedstream without significant conversion of acyclic monoolefin to saturates and recovering said acyclic monoolefin feedstream substantially reduced in said undesirable materials.

9. A process for hydrotreating an acyclic monoolefin feedstream containing undesirable materials including acetylenic compounds, organic sulfur compounds, carbonyl compounds, diolefins, and other unsaturated impurities to selectively hydrogenate said undesirable materials which comprises contacting hydrogen and said feedstream under hydrogenation conditions and in the presence of added carbon monoxide with a catalyst consisting essentially of an arsenide of nickel, iron or cobalt at an elevated temperature sufficient to selectively hydrogenate and remove a substantial portion of said undesirable materials present in said feedstream without significant conversion of acyclic monoolefin to saturates and recovering said acyclic monoolefin feedstream substantially reduced in said undesirable materials.

10. A process according to claim 9 in which said catalyst is supported on a material selected from the group consisting of nonacidic gamma-alumina, silica, magnesia, charcoal, calcium aluminate, and natural and synthetic molecular sieves and in which the metal is present on said support in an amount from about 0.1 to about 20 weight percent and the amount of arsenic present ranges from about 0.05 to about 50 weight percent of said catalyst.

11. A process according to claim 9 for hydrotreating feedstreams containing acyclic monoolefins having up to about 15 carbons per molecule and the catalyst is nickel arsenide.

12. A process according to claim 9 wherein feedstream is a heptene feedstream containing organic sulfur compounds and diolefins and the catalyst is nickel arsenide supported on alumina.

13. A process according to claim 1 wherein the contacting includes a temperature of from about 75° F to about 750° F, a pressure of from about atmospheric to about 1,000 psig, and a hydrogen to feed ratio of 0.1 to 1 to 5 to 1, and the contacting is effected under vapor phase conditions.

* * * * *